US011981719B2

(12) United States Patent
Park et al.

(10) Patent No.: US 11,981,719 B2
(45) Date of Patent: May 14, 2024

(54) GROWTH HORMONE RECEPTOR ANTAGONISTS AND FUSION PROTEINS THEREOF

(71) Applicant: Alteogen, Inc., Daejeon (KR)

(72) Inventors: Soon Jae Park, Daejeon (KR); Jaehyeong Ko, Daejeon (KR); Sun-Ah You, Daejeon (KR); Sang Hoon Yun, Daejeon (KR)

(73) Assignee: Alteogen, Inc., Daejeon (KR)

(*) Notice: Subject to any disclaimer, the term of this patent is extended or adjusted under 35 U.S.C. 154(b) by 111 days.

(21) Appl. No.: 16/954,902

(22) PCT Filed: Dec. 20, 2018

(86) PCT No.: PCT/KR2018/016311
§ 371 (c)(1),
(2) Date: Jun. 17, 2020

(87) PCT Pub. No.: WO2019/125002
PCT Pub. Date: Jun. 27, 2019

(65) Prior Publication Data
US 2020/0399340 A1   Dec. 24, 2020

(30) Foreign Application Priority Data

Dec. 20, 2017 (KR) .................. 10-2017-0176493
Nov. 26, 2018 (KR) .................. 10-2018-0147700

(51) Int. Cl.
| *A61K 38/00* | (2006.01) |
| *A61K 47/62* | (2017.01) |
| *C07K 14/61* | (2006.01) |
| *C07K 14/81* | (2006.01) |

(52) U.S. Cl.
CPC .............. *C07K 14/61* (2013.01); *A61K 47/62* (2017.08); *C07K 14/8125* (2013.01); *A61K 38/00* (2013.01); *C07K 2319/00* (2013.01)

(58) Field of Classification Search
CPC ........ A61K 38/00; A61K 47/62; C07K 14/61; C07K 14/72; C07K 14/8125; C07K 2319/00; C07K 2319/61; C07K 14/81; C07K 2319/31
See application file for complete search history.

(56) References Cited

U.S. PATENT DOCUMENTS

| 5,849,535 A | * | 12/1998 | Cunningham | ............ | A61P 3/10 |
| | | | | | 435/243 |
| 2016/0143999 A1 | | 5/2016 | Tachas | | |
| 2017/0007711 A1 | | 1/2017 | Brody | | |

FOREIGN PATENT DOCUMENTS

| JP | 2005-021157 A | 1/2005 | | |
| JP | 2015506951 A | 3/2015 | | |
| JP | 2015518882 A | 7/2015 | | |
| KR | 10-2013-0029713 A | 3/2013 | | |
| KR | 10-2013-0136883 A | 12/2013 | | |
| KR | 10-1460266 B1 | 11/2014 | | |
| KR | 101460266 B1 | * 11/2014 | ............. | A61K 47/68 |
| WO | WO-2004093913 A1 | * 11/2004 | ........... | A61K 31/585 |
| WO | WO-2005047336 A1 | * 5/2005 | ............. | A61K 47/68 |
| WO | WO 2005/075021 A2 | 8/2005 | | |

OTHER PUBLICATIONS

English translation of KR101460266B1 obtained by Google patent (Year: 2014).*
Ahmed, S. et al. (1999). "Outcome of transphenoidal surgery for acromegaly and its relationship to surgical experience," Clin. Endocrinol. (Oxf.). 50:561-567.
Barkan, A.L. et al. (1997). "Pituitary irradiation is ineffective in normalizing plasma insulin-like growth factor I in patients with acromegaly," J. Clin. Endocrinol. Metab. 82:3187-3191.
Bazan, J.F. (1990). "Haemopoietic receptors and helical cytokines," Immunol. Today 11:350-354.
Bendele, A. et al. (1998). "Short communication: renal tubular vacuolation in animals treated with polyethylene-glycol-conjugated proteins," Toxicol. Sci. 42 (1998) 152-157.
Casanueva, F.F. (1992). "Physiology of growth hormone secretion and action," Endocrinol. Metab. Clin. North Am. 21:483-517.
Elliott, V.L. et al. (2012). "Evidence for metabolic cleavage of a Pegylated protein in vivo using multiple analytical methodologies," Mol. Pharm. 9:1291-1301.
Garay, R.P. et al. (2012). "Antibodies against polyethylene glycol in healthy subjects and in patients treated with PEG-conjugated agents," Expert Opin. Drug Deliv. 9:1319-1323.
Goffin, V. et al. (2000). "Pegvisomant. Pharmacia," Curr. Opin. Investig. Drugs Lond. Engl. 3:752-757. Abstract Only.
Jevsevar, S. et al. (2010). "Pegylation of therapeutic proteins," Biotechnol. J. 5:113-128.
Kopchick, J.J. et al. (2002). "Growth Hormone Receptor Antagonists: Discovery, Development, and Use in Patients with Acromegaly," Endocr. Rev. 23:623-646.
Li, H. et al. (1998). "Growth hormone and insulin-like growth factor I induce bone morphogenetic proteins 2 and 4: a mediator role in bone and tooth formation?" Endocrinology 139:3855-3862.

(Continued)

*Primary Examiner* — Aradhana Sasan
*Assistant Examiner* — Mercy H Sabila
(74) *Attorney, Agent, or Firm* — Cooley LLP

(57) ABSTRACT

The present invention relates to a growth hormone receptor antagonist comprising a growth hormone variant which is modified by substitution of one or more amino acids of growth hormone. Further, the growth hormone receptor antagonist of the present invention may further comprise a long-acting carrier which is fused to the growth hormone variant. The growth hormone receptor antagonist may have strong binding potency to growth hormone receptor and may exhibit a long-lasting antagonistic action.

15 Claims, 6 Drawing Sheets

Specification includes a Sequence Listing.

(56) References Cited

OTHER PUBLICATIONS

Muller, A.F. et al. (2004). "Growth Hormone Receptor Antagonists," J. Clin. Endocrinol. Metab. 89:1503-1511.
Ross, R.J.M. et al. (2001). "Binding and functional studies with the growth hormone receptor antagonist, B2036-PEG (pegvisomant), reveal effects of pegylation and evidence that it binds to a receptor dimer," J. Clin. Endocrinol. Metab. 86:1716-1723.
Swearingen, B. et al. (1999). "Long-term mortality after transsphenoidal surgery and adjunctive therapy for acromegaly," J. Clin. Endocrinol. Metab. 83:3419-3426.
Thorner, M.O. et al. (1999). "Growth hormone (GH) receptor blockade with a PEG-modified GH (B2036-PEG) lowers serum insulin-like growth factor-I but does not acutely stimulate serum GH," J. Clin. Endocrinol. Metab. 84:2098-2103.
Van der Lely, A.J. et al. (1997). "The role of radiotherapy in acromegaly," J. Clin. Endocrinol. Metab. 82:3185-3186.

\* cited by examiner

[FIG. 1]
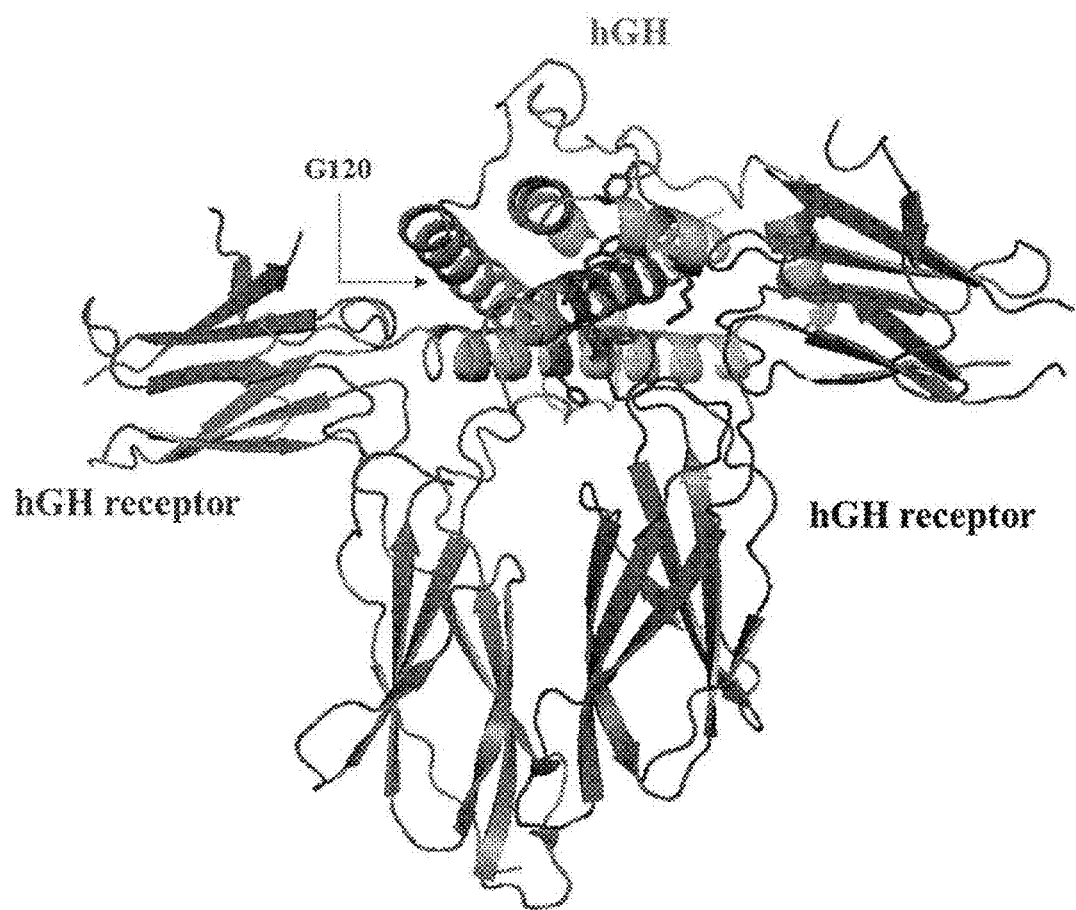

[FIG. 2]
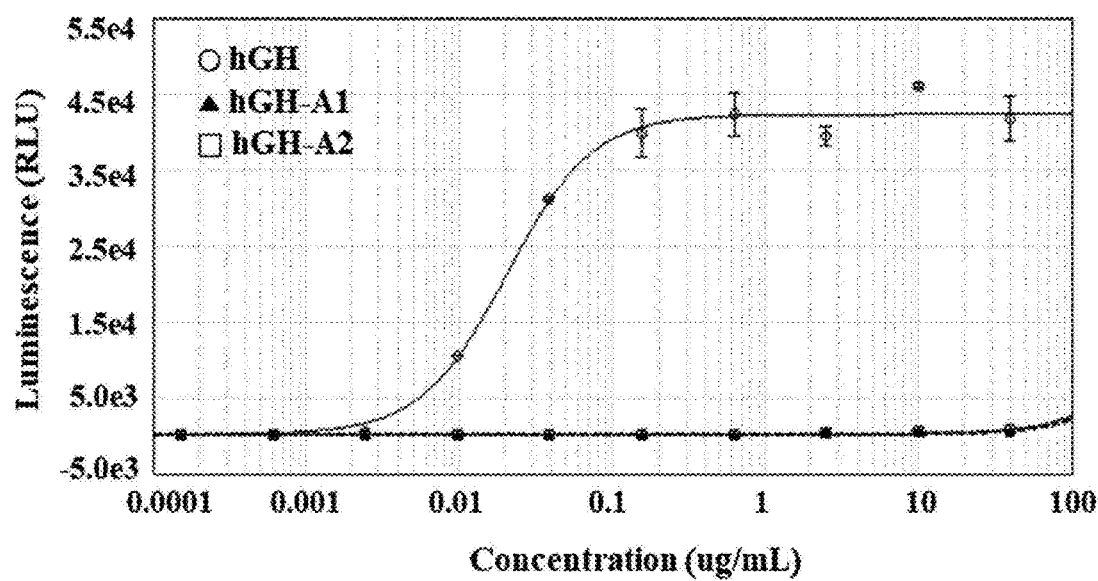

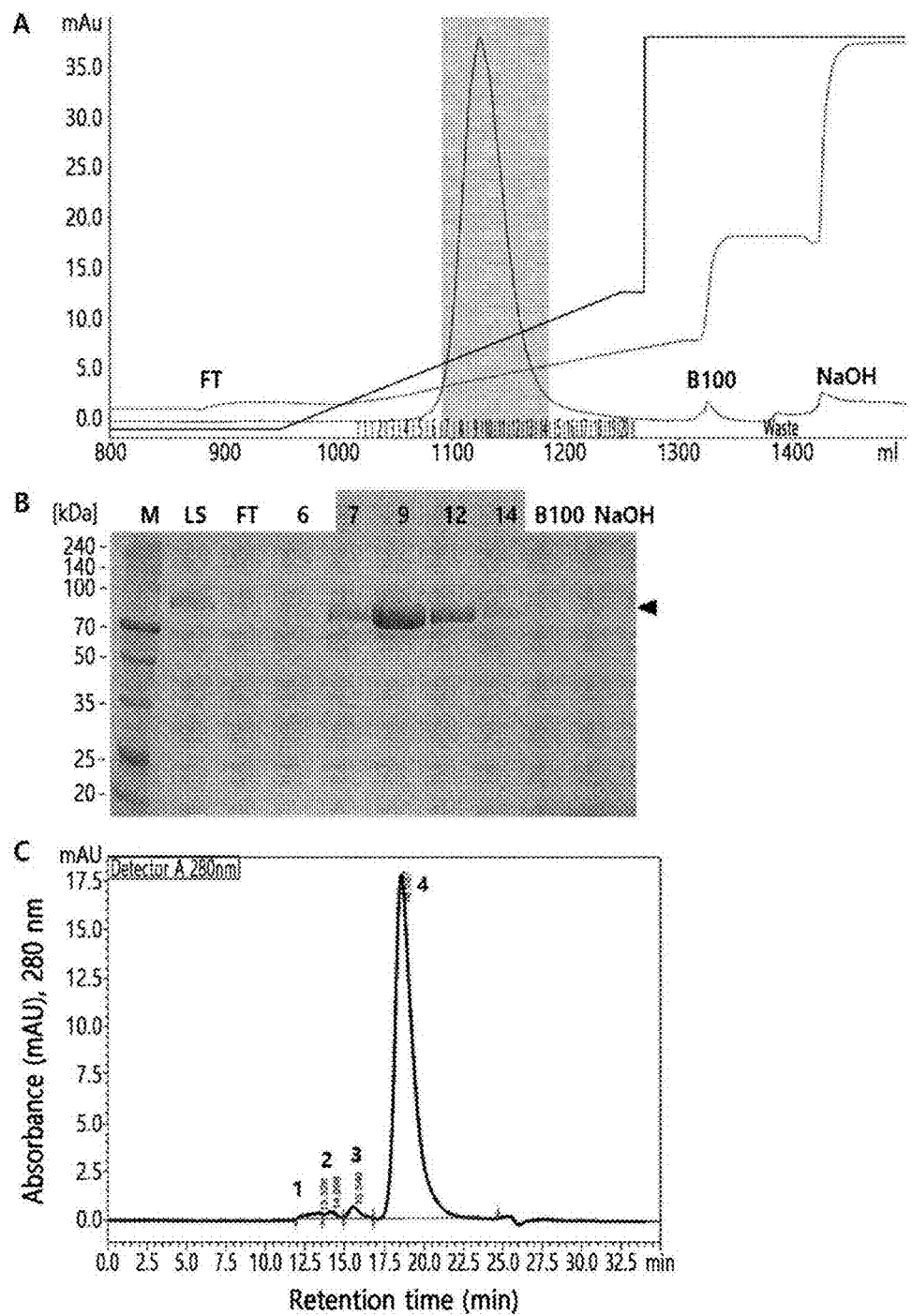
[FIG. 3]

[FIG. 4]
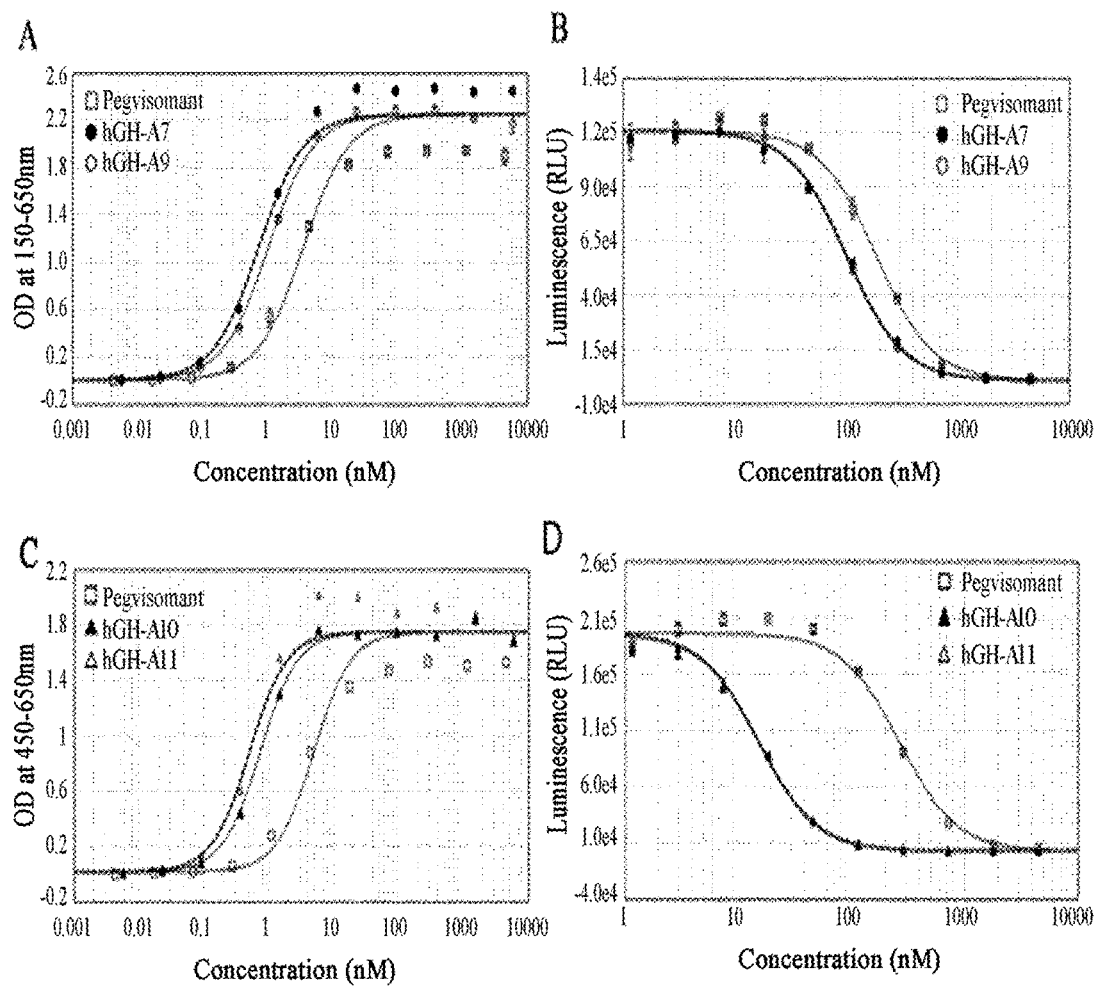

[FIG. 5]
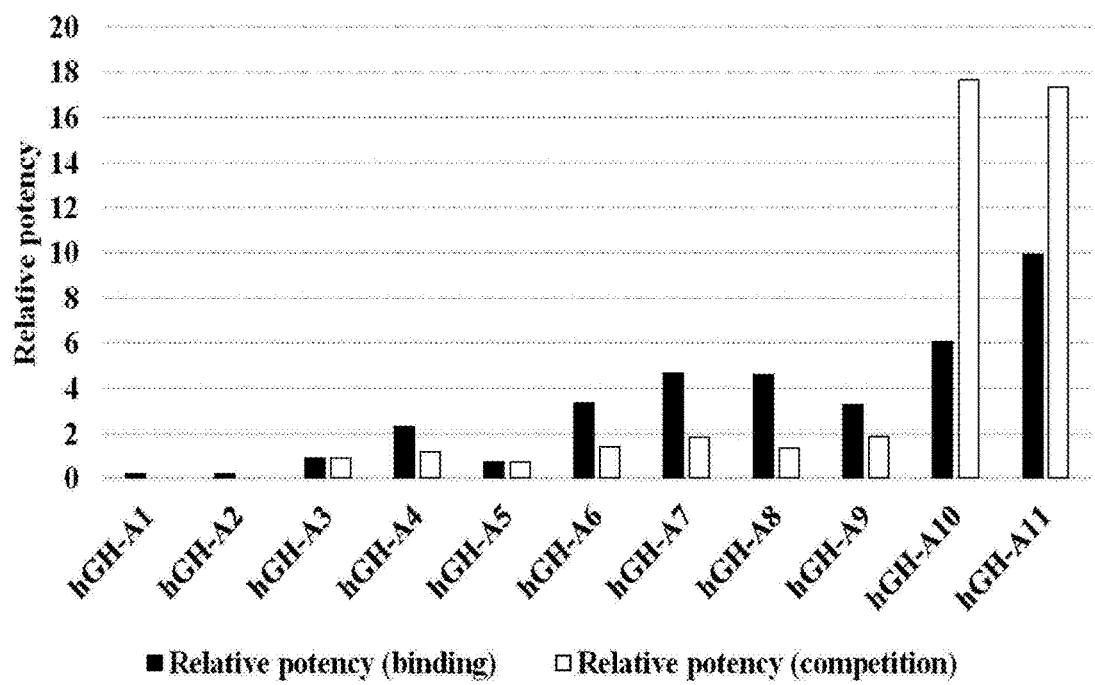

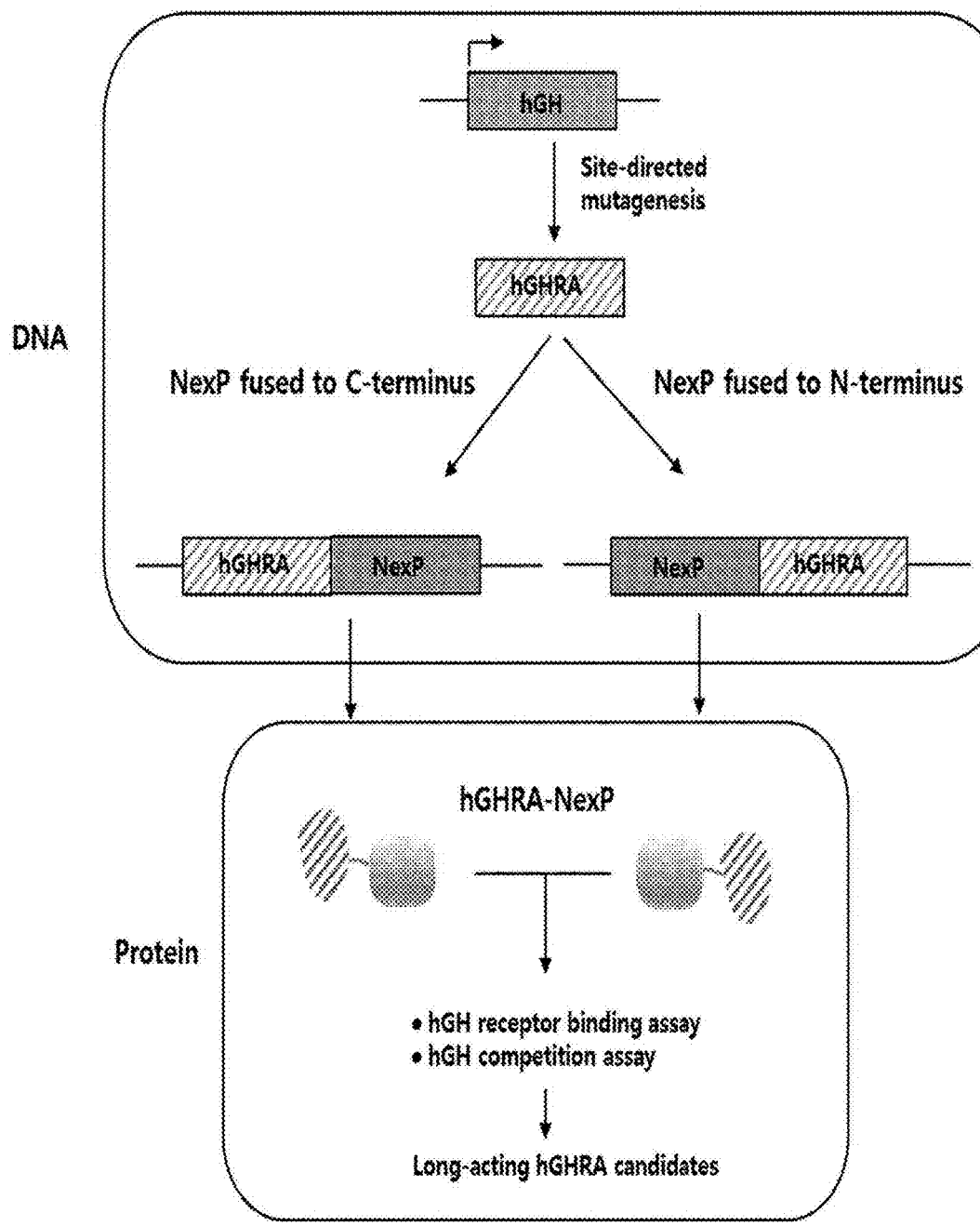
[FIG. 6]

GROWTH HORMONE RECEPTOR ANTAGONISTS AND FUSION PROTEINS THEREOF

CROSS REFERENCE TO RELATED APPLICATIONS

This application is a U.S. national phase application of International PCT Patent Application No. PCT/KR2018/016311, which was filed on Dec. 20, 2018, which claims priority to Korean Patent Application No. 10-2018-0147700, filed Nov. 26, 2018, and Korean Patent Application No. 10-2017-0176493, filed Dec. 20, 2017. These applications are incorporated herein by reference in their entireties.

STATEMENT REGARDING SEQUENCE LISTING

The instant application contains a Sequence Listing which has been submitted in ASCII format via EFS-Web and is hereby incorporated by reference in its entirety. Said ASCII copy, created on Aug. 10, 2022 is named "HANO_063_00US_ST25.txt" and is 18,475 bytes in size.

BACKGROUND OF THE INVENTION

1. Field of the Invention

The present invention relates to a growth hormone receptor antagonist comprising a growth hormone variant in which one or more amino acids in an amino acid sequence of growth hormone are substituted with another amino acid.

2. Description of the Related Art

Growth hormone is an endocrine hormone that promotes growth. Human growth hormone (hGH) is secreted by the pituitary gland and acts on various tissues including the liver. It binds to the extracellular domain of human growth hormone receptor (hGHR), which belongs to a class I cytokine receptor superfamily forming a dimer in complex with hGH (J. F. Bazan, Haemopoietic receptors and helical cytokines, Immunol. Today. 11 (1990) 350-354), and subsequent signal transduction increases expression of insulin-like growth factor I (IGF-1) (F. F. Casanueva, Physiology of growth hormone secretion and action, Endocrinol. Metab. Clin. North Am. 21 (1992) 483-517; H. Li, P. M. Bartold, C. Z. Zhang, R. W. Clarkson, W. G. Young, M. J. Waters, Growth hormone and insulin-like growth factor I induce bone morphogenetic proteins 2 and 4: a mediator role in bone and tooth formation, Endocrinology. 139 (1998) 3855-3862. doi:10.1210/endo.139.9.6211).

Excessive secretion of hGH and resulting elevation of IGF-1 cause acromegaly, a chronic disorder having a typical symptom of enlarged hands and feet. Treatment strategies for acromegaly include surgical removal of the cancerous pituitary gland, radiotherapy, and administration of dopamine agonist. However, there is a group of patients who do not respond to surgical treatment (B. Swearingen, F. G. Barker, L. Katznelson, B. M. Biller, S. Grinspoon, A. Klibanski, N. Moayeri, P. M. Black, N. T. Zervas, Long-term mortality after transsphenoidal surgery and adjunctive therapy for acromegaly, J. Clin. Endocrinol. Metab. 83 (1998) 3419-3426; S. Ahmed, M. Elsheikh, I. M. Stratton, R. C. Page, C. B. Adams, J. A. Wass, Outcome of transphenoidal surgery for acromegaly and its relationship to surgical experience, Clin. Endocrinol. (Oxf.). 50 (1999) 561-567), and radiotherapy shows delayed effect as well as poor effect (A. L. Barkan, I. Halasz, K. J. Dornfeld, C. A. Jaffe, R. D. Friberg, W. F. Chandler, H. M. Sandler, Pituitary irradiation is ineffective in normalizing plasma insulin-like growth factor I in patients with acromegaly, J. Clin. Endocrinol. Metab. 82 (1997) 3187-3191. doi:10.1210/jcem.82.10.4249; A. J. van der Lely, W. W. de Herder, S. W. Lamberts, The role of radiotherapy in acromegaly, J. Clin. Endocrinol. Metab. 82 (1997) 3185-3186. doi:10.1210/jcem.82.10.4325). hGH receptor antagonist (hGHRA) is an alternative treatment option because it prevents hGH from binding to the hGH receptor by occupying the hGH receptor instead of hGH (J. J. Kopchick, C. Parkinson, E. C. Stevens, P. J. Trainer, Growth Hormone Receptor Antagonists: Discovery, Development, and Use in Patients with Acromegaly, Endocr. Rev. 23 (2002) 623-646. doi:10.1210/er.2001-0022; A. F. Muller, J. J. Kopchick, A. Flyvbjerg, V. D. Lely, A. Jan, Growth Hormone Receptor Antagonists, J. Clin. Endocrinol. Metab. 89 (2004) 1503-1511. doi:10.1210/jc.2002-022049).

hGHRA capable of lasting for a long time inside the human body improves patients' quality of life by reducing the dosing frequency. Pegvisomant, a pegylated version of hGH antagonist has been developed for the purpose and commercialized on market (M. O. Thorner, C. J. Strasburger, Z. Wu, M. Straume, M. Bidlingmaier, S. S. Pezzoli, K. Zib, J. C. Scarlett, W. F. Bennett, Growth hormone (GH) receptor blockade with a PEG-modified GH (B2036-PEG) lowers serum insulin-like growth factor-I but does not acutely stimulate serum GH, J. Clin. Endocrinol. Metab. 84 (1999) 2098-2103. doi:10.1210/jcem.84.6.5732; V. Goffin, P. Touraine, Pegvisomant. Pharmacia, Curr. Opin. Investig. Drugs Lond. Engl. 2000. 3 (2002) 752-757). Long-acting mechanism of Pegvisomant is to link a polyethylene glycol polymer to a therapeutic protein to increase its molecular size so that it remains in the bloodstream without being filtered by the kidney (R. J. Ross, K. C. Leung, M. Maamra, W. Bennett, N. Doyle, M. J. Waters, K. K. Ho, Binding and functional studies with the growth hormone receptor antagonist, B2036-PEG (pegvisomant), reveal effects of pegylation and evidence that it binds to a receptor dimer, J. Clin. Endocrinol. Metab. 86 (2001) 1716-1723. doi:10.1210/jcem.86.4.7403). Another aspect of Pegylation protects proteins from proteolytic enzymes (S. Jevsevar, M. Kunstelj, V. G. Porekar, Pegylation of therapeutic proteins, Biotechnol. J. 5 (2010) 113-128. doi:10.1002/biot.200900218). However, pegylation of therapeutic proteins may limit their usefulness. The Pegylation process requires a series of chemical reactions, which are not cost effective and reaction products are generally not homogeneous. As a result, it requires further purification steps that usually is not easily accomplished. Pegylated proteins are also shown to be safe when small polyethylene glycols (e.g. 5 kDa) are used, but safety issues are still suggested, as in animal studies that reported renal vacuolation as well as the appearance of antibodies against pegylation. Furthermore, Pegylated proteins tend to have lower binding affinity to protein receptors than their original proteins (R. P. Garay, R. El-Gewely, J. K. Armstrong, G. Garratty, P. Richette, Antibodies against polyethylene glycol in healthy subjects and in patients treated with PEG-conjugated agents, Expert Opin. Drug Deliv. 9 (2012) 1319-1323. doi:10.1517/17425247.2012.720969; A. Bendele, J. Seely, C. Richey, G. Sennello, G. Shopp, Short communication: renal tubular vacuolation in animals treated with polyethylene-glycol-conjugated proteins, Toxicol. Sci. Off. J. Soc. Toxicol. 42 (1998) 152-157. doi:10.1006/toxs.1997.2396; V. L. Elliott, G. T. Edge, M. M. Phelan, L.-Y. Lian, R. Webster, R. F. Finn, B. K. Park, N. R. Kitteringham, Evidence for metabolic cleavage of a Pegylated protein in vivo using multiple analytical methodologies, Mol. Pharm. 9 (2012) 1291-1301. doi:10.1021/mp200587m). Accordingly, there is a need for an alternative technique for hGHRA that lasts for a long period of time and particularly has high binding affinity to the receptor to exhibit high inhibitory potency. In addition, a cost-effective and simple process is required.

Under this background, the present inventors have designed a novel growth hormone receptor antagonist hGHRA that lasts for a long period of time and exhibits a strong inhibitory potency against the growth hormone receptor, and characterized the same in vitro, thereby completing the present invention.

SUMMARY OF THE INVENTION

An object of the present invention is to provide a growth hormone receptor antagonist comprising a growth hormone variant in which one or more amino acids in an amino acid sequence of growth hormone are substituted with another amino acid.

Another object of the present invention is to provide a pharmaceutical composition for preventing or treating a disease which is caused by human growth hormone, the pharmaceutical composition comprising the growth hormone receptor antagonist.

Still another object of the present invention is to provide a method of preparing the growth hormone receptor antagonist.

DETAILED DESCRIPTION OF THE PREFERRED EMBODIMENTS

Hereinafter, the present invention will be described in more detail.

Meanwhile, each description and embodiment disclosed herein may also be applied to other descriptions and embodiments. That is, all combinations of various elements disclosed herein fall within the scope of the present invention. Further, the scope of the present invention is not limited by the specific description described below.

Further, those skilled in the art will recognize, or be able to ascertain using no more than routine experimentation, many equivalents to the specific embodiments of the invention described herein. Further, these equivalents should be interpreted to fall within the present invention.

To achieve the above objects, an aspect of the present invention provides a growth hormone receptor antagonist comprising a growth hormone variant in which one or more amino acids in an amino acid sequence of growth hormone are substituted with another amino acid.

As used herein, the term 'growth hormone' refers to a peptide hormone that is secreted by the pituitary gland to stimulate body growth, and has a function of metabolism regulation, in addition to stimulation of body growth. The growth hormone may be specifically human growth hormone (hGH), and hGH is consisting of 191 amino acids, as known.

As used herein, the term 'growth hormone variant' means that one or more amino acids in an amino acid sequence of growth hormone are substituted with another amino acid. In other words, it refers to a growth hormone having substitution of one or more amino acids.

Specifically, the substitution may comprise substitution of the $120^{th}$ amino acid (more specifically, substitution with lysine or arginine) in the amino acid sequence of growth hormone. Further, the substitution may comprise substitution of the $46^{th}$ amino acid (more specifically, substitution with lysine).

Further, the substitution may comprise substitution of the $174^{th}$ amino acid (more specifically, substitution with serine) and substitution of the $21^{st}$ amino acid (more specifically, substitution with asparagine) in the amino acid sequence of growth hormone.

Specifically, the substitution may comprise substitution at one or more positions selected from the group consisting of the $18^{th}$ amino acid, the $21^{st}$ amino acid, the $46^{th}$ amino acid, the $54^{th}$ amino acid, the $64^{th}$ amino acid, the $120^{th}$ amino acid, the $167^{th}$ amino acid, the $168^{th}$ amino acid, the $171^{st}$ amino acid, the $172^{nd}$ amino acid, the $174^{th}$ amino acid, the $176^{th}$ amino acid, and the $179^{th}$ amino acid in the amino acid sequence.

More specifically, the substitution may comprise one or more substitutions selected from the group consisting of H18D, H21N, Q46K, F54P, R64K, G120K, R167N, K168A, D171S, K172R, E174S, F176Y, and I179T in the amino acid sequence of growth hormone.

If desired, the variant may be modified by phosphorylation, sulfation, acrylation, glycosylation, methylation, farnesylation, acetylation, amidation, etc.

For non-limiting example in the present invention, the growth hormone variant may be a protein having SEQ ID NO. as in the following Table 1. The growth hormone variants of SEQ ID NOS: 1 to 9 are the same as growth hormone variants included in Examples 1 to 9 described below, respectively. Meanwhile, Example 10 and Example 11 include growth hormone variants of SEQ ID NO: 7 and SEQ ID NO: 9, respectively.

TABLE 1

SEQ ID NO: 1  FPTIPLSRLFDNAMLRAHRLHQLAFDTYQEFEEAYIPKEQKYSFLQNPQTSLCFSESIPTP
              SNREETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFRKDMDKVETFLRIVQCR
              SVEGSCGF

SEQ ID NO: 2  FPTIPLSRLFDNAMLRAHRLHQLAFDTYQEFEEAYIPKEQKYSFLQNPQTSLCFSESIPTP
              SNREETQQKSNLELLRISLLLIQSWLEPVQFLRSVFANSLVYGASDSNVYDLLKDLEERIQ
              TLMGRLEDGSPRTGQIFKQTYSKFDTNSHNDDALLKNYGLLYCFRKDMDKVETFLRIVQCR
              SVEGSCGF

SEQ ID NO: 3  FPTIPLSRLFDNAMLRAHRLNQLAFDTYQEFEEAYIPKEQKYSFLQNPQTSLCFSESIPTP
              SNREETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFRKDMDKVSTFLRIVQCR
              SVEGSCGF

TABLE 1-continued

```
SEQ ID NO: 4  FPTIPLSRLFDNAMLRADRLNQLAFDTYQEFEEAYIPKEQKYSFLQNPQTSLCFSESIPTP
              SNREETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFRKDMDKVSTFLRTVQCR
              SVEGSCGF

SEQ ID NO: 5  FPTIPLSRLFDNAMLRAHRLNQLAFDTYQEFEEAYIPKEQKYSFLQNPQTSLCFSESIPTP
              SNREETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFRKDMDKVSTYLRIVQCR
              SVEGSCGF

SEQ ID NO: 6  FPTIPLSRLFDNAMLRAHRLNQLAFDTYQEFEEAYIPKEQKYSFLQNPQTSLCPSESIPTP
              SNKEETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFRKDMDKVSTYLRIVQCR
              SVEGSCGF

SEQ ID NO: 7  FPTIPLSRLFDNAMLRAHRLNQLAFDTYQEFEEAYIPKEQKYSFLQNPQTSLCPSESIPTP
              SNKEETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFNKDMSKVSTYLRIVQCR
              SVEGSCGF

SEQ ID NO: 8  FPTIPLSRLFDNAMLRADRLNQLAFDTYQEFEEAYIPKEQKYSFLQNPQTSLCFSESIPTP
              SNREETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFNADMSRVSTFLRTVQCR
              SVEGSCGF

SEQ ID NO: 9  FPTIPLSRLFDNAMLRADRLNQLAFDTYQEFEEAYIPKEQKYSFLKNPQTSLCFSESIPTP
              SNREETQQKSNLELLRISLLLIQSWLEPVQFLRSVFANSLVYGASDSNVYDLLKDLEEKIQ
              TLMGRLEDGSPRTGQIFKQTYSKFDTNSHNDDALLKNYGLLYCFRKDMDKVSTFLRTVQCR
              SVEGSCGF
```

As used herein, the term 'growth hormone receptor (GHR)' refers to a receptor to which growth hormone binds to transmit signals into cells. The growth hormone receptor has a structure of penetrating the cell membrane once. When the receptor is activated, STAT dimers regulate transcription of various genes inside the nucleus through JAK/STAT pathway. Growth hormone receptors are found in tissues throughout the body, including liver, muscle, fat, kidney, early embryo, fetal tissue, etc.

When growth hormone binds to the receptor, subsequent signaling leads to increased secretion of IGF (insulin like growth factor)-1. Excessive secretion of hGH and resulting elevation of IGF-1 may cause acromegaly which is a chronic disease having a typical symptom of enlarged hands and feet.

As used herein, the term 'growth hormone receptor antagonist' refers to an agent that antagonizes binding of growth hormone to the growth hormone receptor, thereby suppressing side effects caused by excessive binding of growth hormone to the growth hormone receptor.

Specifically, the growth hormone receptor antagonist may be a growth hormone variant having high binding potency to the growth hormone receptor and capable of competitively antagonizing the efficacy of growth hormone.

Further, the growth hormone receptor antagonist may comprise a long-acting carrier fused to the growth hormone variant.

As used herein, the term 'long-acting carrier' refers to a substance capable of increasing in vivo half-life. When a variety of long-acting carriers known to increase in vivo half-life are fused to the growth hormone variant according to the present invention, it is expected to be used as a long-acting agent having increased in vivo half-life while antagonizing the growth hormone receptor.

In the present invention, non-limiting examples of the long-acting carrier may comprise various carriers capable of reducing renal clearance, specifically, any one or more selected from the group consisting of polyethylene glycol, fatty acids, albumin or fragments thereof, albumin-binding substances, alpha-1 antitrypsin or variants thereof, immunoglobulin Fc or fragments thereof, a polymer of repeating units of a specific amino acid sequence, antibodies or fragments thereof, FcRn-binding substances, in vivo connective tissues or derivatives thereof, nucleotides, fibronectin, transferrin, saccharides, and polymers.

More specifically, alpha-1 antitrypsin (A1AT) or a variant thereof may be used as the long-acting carrier.

The alpha-1 antitrypsin or variant thereof is disclosed in Patent Publication NOS. KR 10-2013-0136883 A and KR 10-2013-0029713 A. Specifically, A1AT is one of the most abundant proteins in human plasma at a concentration of 1.5-3.5 gram per 1 liter, and is mainly synthesized in hepatocytes and secreted into the blood. The alpha-1 antitrypsin variant was designed by including additional mutations in A1AT to increase glycosylation and to eliminate its intrinsic activity. The alpha-1 antitrypsin variant may be fused to a target protein to prolong the half-life of the target protein.

One of the major benefits of the alpha-1 antitrypsin variant technology is non-immunogenic. In particular, the plasma-derived human A1AT has already been used as a therapeutic agent for patients with emphysema, which is a lung disease, due to A1AT deficiency. Its weekly dose is as very high as 60 mg/kg body weight. Serious side effects have not yet been reported, indicating the safety of A1AT as a therapeutic agent.

In the present invention, non-limiting example of the growth hormone receptor antagonist may provide a long-lasting hGHRA obtained by fusing the alpha-1 antitrypsin variant to the growth hormone variant. The alpha-1 antitrypsin variant may comprises substitution of one or more amino acids among the 1$^{st}$ and 25$^{th}$ amino acids in the sequence of the alpha-1 antitrypsin, and the growth hormone variant may comprise any one or more substitutions selected from H18D, H21N, Q46K, F54P, R64K, G120K, R167N, K168A, D171S, K172R, E174S, F176Y, and I179T in the amino acid sequence of the growth hormone.

More specifically, the alpha-1 antitrypsin variant may have, for example, an amino acid sequence of SEQ ID NO: 10 of the following Table 2. The alpha-1 antitrypsin variant may be "NexP" (KR 10-2013-0136883 A).

TABLE 2

| | |
|---|---|
| SEQ ID NO: 10 | EDPQGDAANKTDTSHHDQDHPTFNKITPNLAEFAFSLYRQLAHQSNSTNIFFSPVSIATAFAMLSL |
| | GTKADTHDEILEGLNFNLTEIPEAQIHEGFQELLHTLNQPDSQLQLTTGNGLFLSEGLKLVDKFLE |
| | DVKKLYHSEAFTVNFGDTEEAKKQINDYVEKGTQGKIVDLVKELDRDTVFALVNYIFFKGKWERPF |
| | EVKDTEEEDFHVDQVTTVKVPMMKRLGMFNIQHCKKLSSWVLLMKYLGNATAIFFLPDEGKLQHLE |
| | NELTHDIITKFLENEDRRSASLHLPKLSITGTYDLKSVLGQLGITKVFSNGADLSGVTEEAPLKLS |
| | KAVHKAVLTIDEKGTEAAGAMFLEAINMSIPPEVKFNKPFVFLMIDQNTKSPLFMGKVVNPTQK |

The growth hormone receptor antagonist obtained by fusing the alpha-1 antitrypsin variant to the growth hormone variant in order to increase the half-life in the blood plasma may have high binding potency to the growth hormone receptor and may strongly antagonize the efficacy of growth hormone, as compared with a Pegylated growth hormone variant.

Specifically, Examples 4, 6, 7, 8, 9, 10, and 11 which are non-limiting examples of the growth hormone receptor antagonist in the present invention showed high binding potency to hGH receptor and high inhibitory potency, as compared with Pegvisomant which is a known growth hormone receptor antagonist (see FIGS. 4 and 5, Table 4)

In the growth hormone receptor antagonist obtained by fusing the long-acting carrier to the growth hormone variant, the long-acting carrier may be fused to the N-terminus or the C-terminus of the growth hormone variant.

Particularly, a growth hormone receptor antagonist obtained by fusing a long-acting carrier to the N-terminus of a specific growth hormone variant may have remarkably high binding potency to the growth hormone receptor or may strongly antagonize the efficacy of growth hormone, as compared with that obtained by fusing the long-acting carrier to the C-terminus thereof. For non-limiting example in the present invention, even though hGH-A10 and hGH-A11 have the growth hormone variant of the same amino acid sequence as hGH-A7 and hGH-A9, respectively, those fused to the N-terminus of the variant were confirmed to strongly antagonize the efficacy of growth hormone (see FIGS. 4C and 4D, FIG. 5, and Table 4).

In the present invention, the long-acting carrier may be fused to the growth hormone variant directly or via a linker.

Any linker may be used without limitation, as long as it is used in a covalent bond between the long-acting carrier and the growth hormone variant and it does not influence the activity. Specifically, the linker may be a non-peptidyl linker of polyethylene glycol, polypropylene glycol, a copolymer of ethylene glycol and propylene glycol, polyoxyethylated polyol, polyvinyl alcohol, polysaccharide, dextran, polyvinyl ethyl ether, polylactic acid (PLA), polylactic-glycolic acid (PLGA), a lipid polymer, chitins, hyaluronic acid, or a combination thereof, and may be a peptidyl linker in which two or more amino acid are linked. A non-limiting example may include GGGGS, and a linker (2X, 3X, 4X, etc.) with a variable length.

To achieve the above objects, another aspect of the present invention provides a pharmaceutical composition for preventing or treating a disease which is caused by human growth hormone, the pharmaceutical composition comprising the growth hormone receptor antagonist. The terms used herein are the same as described above.

As used herein, the term 'disease which is caused by human growth hormone' refers to a disease caused by excess growth hormone secretion due to abnormal control of the pituitary gland, etc. For example, the disease may include acromegaly, gigantism, cancer, diabetic nephropathy, arthritis, lung inflammation, growth hormone deficiency (GHD), idiopathic short stature, Turner's syndrome, Prader-Willi syndrome, small for gestational age, chronic renal insufficiency (CRI), etc.

Further, the disease caused by human growth hormone includes a disease caused by increased secretion of IGF (insulin like growth factor)-1 due to excessive action of growth hormone.

For non-limiting example in the present invention, Examples (hGH-A1 to hGH-A11) suppress binding of growth hormone to a receptor thereof, thereby being used for the prevention or treatment of a disease caused by human growth hormone (see Experimental Example and Table 4).

To achieve the above objects, still another aspect of the present invention provides a method of preparing the growth hormone receptor antagonist, comprising the step of culturing cells comprising a polynucleotide encoding the growth hormone variant in which one or more amino acids in the amino acid sequence of growth hormone are substituted with another amino acid. The terms used herein are the same as described above.

The cells may be cells transfected with an expression vector of the growth hormone variant, and non-limiting example thereof may include CHO (Chinese hamster ovary)-K1, etc.

To achieve the above objects, still another aspect of the present invention provides a method of preventing or treating the disease caused by human growth hormone, the method including the step of administering, to a subject, the pharmaceutical composition including the growth hormone receptor antagonist. The terms used herein are the same as described above.

As used herein, the term "administering" means introducing the pharmaceutical composition of the present invention into a patient by any appropriate method, and administration of the composition of the present invention may be performed via various routes such as oral or parenteral route, as long as it is able to reach a desired tissue. The agent according to the present invention may be prepared into various formulations according to the desired mode of administration.

The administration may be prophylactically or therapeutically performed.

The administration frequency of the agent of the present invention is not particularly limited, but it may be administered once a day or several times in divided doses.

A subject to be administered with the agent according to the present invention may refer to all animals including humans. The animals may include mammals, such as cattle, horses, sheep, pigs, goats, camels, antelopes, dogs, cats, etc., which need treatment of similar symptoms, as well as humans, but are not limited thereto.

To achieve the above objects, still another aspect of the present invention provides use of the pharmaceutical composition comprising the growth hormone receptor antagonist in the prevention or treatment of the disease caused by human growth hormone. The terms used herein are the same as described above.

Effect of the Invention

A growth hormone receptor antagonist according to the present invention may have a strong binding potency to growth hormone receptor and may exhibit a long-lasting antagonistic action.

BRIEF DESCRIPTION OF THE DRAWINGS

FIG. 1 shows a structure of a complex of growth hormone and growth hormone receptor (PDB id: 3HHR);

FIG. 2 shows hGH efficacy on hGH, hGH-A1, and hGH-A2;

FIG. 3 shows chromatography purification of hGHR-A3 which is a growth hormone receptor antagonist of the present invention, in which FIG. 3A shows a chromatogram of second ion-exchange column chromatography for purification of hGHR-A3, FIG. 3B shows the result of 10% SDS-polyacrylamide gel electrophoresis of each purification fraction, and FIG. 3C shows purity of purified hGHR-A3, as analyzed by size-exclusion HPLC;

FIG. 4 shows the results of hGH receptor binding assay and hGH competitive inhibition assay for hGH-A7, hGH-A9, hGH-A10, hGH-A11 and Pegvisomant. The results of measuring binding profiles of hGH-A7 (●), hGH-A9 (○), and Pegvisomant (□) are shown in FIG. 4A. Further, the results of measuring binding profiles of hGH-A10 (▲), hGH-A11 (Δ), and Pegvisomant (□) are shown in FIG. 4C. The results of measuring binding profiles of hGH-A7 (●), hGH-A9 (○), and Pegvisomant (□) are shown in FIG. 4B. Further, the results of measuring binding profiles of hGH-A10 (▲), hGH-A11 (Δ), and Pegvisomant (□) are shown in FIG. 4D.

FIG. 5 shows a plot of the results of relative binding potency and hGH competitive efficacy of hGH-A1 to hGH-A11 and Pegvisomant of Comparative Example; and FIG. 6 shows a diagram illustrating a process of preparing the growth hormone receptor antagonist of the present invention.

BEST MODE FOR THE INVENTION

Hereinafter, the present invention will be described in more detail with reference to the following Examples. However, the following Examples are for illustrative purposes only, and the scope of the present invention is not intended to be limited by these Examples.

Preparation Example: Preparation of Growth Hormone Receptor Antagonist

1. Cloning, Transfection, and Cell Culture cDNA clones of hGH-NexP were prepared according to a known method. The hGH receptor antagonists (hGHRA-NexP) were prepared by site-directed mutagenesis of hGH-NexP gene. Afterwards, the mutations were confirmed by DNA sequencing. CHO (Chinese hamster ovary)-K1 cells were transiently transfected with a plasmid containing a nucleotide sequence of each hGHRA-NexP clone. The transfected cells were grown in IMDM medium (Iscove's Modified Dulbecco's Medium) supplemented with 10% FBS in a 5% $CO_2$ humidified incubator for 7 days.

2. Purification of hGBRA-NexP hGHRA-NexP variants were purified from the transiently transfected CHO-K1 cells by a series of column chromatography. The culture supernatant was diluted with an equal volume of buffer A (20 mM sodium phosphate, pH 8.0), and applied to an ion-exchange column equilibrated with buffer A. After a washing step with buffer A, the proteins were eluted with a linear gradient of NaCl in buffer A. Then the fractions containing hGHRA-NexP were directly loaded onto an affinity column equilibrated with buffer B (20 mM Tris-HCl, 100 mM NaCl, pH 7.5), and the fraction was eluted with a gradient of $MgCl_2$ in buffer B. After adjusting pH and conductivity of the elution pool, they were loaded onto a second ion exchange column that was equilibrated with buffer C (20 mM sodium phosphate, 80 mM NaCl, pH 8.0). The protein fraction was concentrated with a Vivaspin 20 concentrator (Sartorius), and dialyzed against phosphate buffer saline (PBS).

3. SE-HPLC Analysis

To determine purity of hGHRA-NexP, size-exclusion high-performance liquid chromatography (SE-HPLC) was performed. The protein solution was loaded onto a TSKgel G3000SWXL column (Tosoh), and a chromatogram was obtained in a running buffer (50 mM sodium phosphate, 150 mM NaCl, 0.05% sodium azide, pH 6.8) at a flow rate of 0.5 mL/min. An area percentage (%) of a main peak of the chromatogram was calculated.

Example: Examples of Growth Hormone Receptor Antagonist

An object of the present invention is to prepare growth hormone receptor antagonists by using site-directed mutagenesis on hGH sequence and a NexP technology to provide for long-acting property, and Example 1 (hGH-A1: G120K) and Example 2 (hGH-A2: G120R), each in which an amino acid at position 120 of hGH was substituted, were prepared. Further, for the above object, additional mutation was introduced into site 1 of hGH-A1 in the hGH sequence to prepare Examples 3 to 7. Specific amino acids substituted in Examples are shown in Table 3 below. In Example 9, Q46K mutation was introduced to induce cation-π interaction through introduction of lysine.

TABLE 3

| Name | Mutations |
| --- | --- |
| Example 1 | hGH-A1 | G120K |
| Example 2 | hGH-A2 | G120R |
| Example 3 | hGH-A3 | H21N/G120K/E174S |
| Example 4 | hGH-A4 | H18D/H21N/G120K/E174S/I179T |
| Example 5 | hGH-A5 | H21N/G120K/E174S/F176Y |

TABLE 3-continued

| | Name | Mutations |
|---|---|---|
| Example 6 | hGH-A6 | H21N/F54P/R64K/G120K/E174S/F176Y |
| Examples 7 and 10 | hGH-A7, hGH-A10 | H21N/F54P/R64K/G120K/R167N/ D171S/E174S/F176Y |
| Example 8 | hGH-A8 | H18D/H21N/G120K/R167N/K168A/ D171S/K172R/E174S/I179T |
| Examples 9 and 11 | hGH-A9, hGH-A11 | H18D/H21N/Q46K/G120K/E174S/I179T |

In Table 3, hGH-A1 to hGH-A9 were obtained by fusing NexP to the C-terminus of the variant, and hGH-A10 and hGH-A11 were obtained by fusing NexP to the N-terminus of the variant.

The hGHRA-NexP proteins were prepared by transfection of CHO-K1 cell and a series of column chromatography according to Preparation Example described above. Representatively, a chromatogram of the second ion exchange column chromatography is shown in FIG. 3A. Pure proteins were obtained from chromatography, and purified proteins were migrated in the position between 100 kDa and 70 kDa (FIG. 3B). After pooling the fractions from fraction number 7 to 14, the solutions were dialyzed against phosphate buffer saline (PBS). It was confirmed that the protein showed high purity of 95%, as shown in the main peak of SE-HPLC chromatogram (FIG. 3C).

Experimental Example: Analysis of hGH Efficacy and Receptor Binding Potency 1. hGH Efficacy Analysis Method For this analysis, hGH receptor gene was introduced into the chromosome of HEK293F cells containing a luciferase gene that could be induced by hGH receptor signaling. The prepared cell line was named as hGHR/Luc/HEK293F. Serial dilutions of hGH and hGHRA-NexP were added to a 96-well white plate containing hGHR/Luc/HEK293F, respectively. This plate was incubated in a 5% $CO_2$ incubator at 37° C. for 24 hours. After incubation, 100 μL of luciferase assay reagent (Steady-Glo® luciferase assay system, Promega) was added to each well, and the plate was wrapped for protection against light. After 5 minutes at room temperature, a multi-mode microplate reader (SpectraMax M5, Molecular Devices) was used to analyze luminescence from wells.

The results of measuring hGH, hGH-A1, and hGH-A2 are shown in FIG. 2. It was confirmed that hGH-A1 and hGH-A2 showed no efficacy, unlike hGH.

2. hGH Receptor Binding Potency Analysis

Binding potency of hGRA-NexP to hGH receptor was evaluated by affinity analysis using a recombinant hGH receptor Fc chimera. A microplate was coated with the hGH receptor chimera at 25° C. overnight, and washed with TPBS buffer (PBS buffer containing 0.05% Tween-20), and samples (Examples 1 to 11 and Pegvisomant) were loaded on each well. The samples were washed three times, and conjugated with anti-hGH-polyclonal antibody-biotin. After additional washing step, 3,3',5,5'-tetramethylbenzidine (TMB) was added to each well to allow TMB reaction. Absorbance signals from the reaction were recorded at 450 nm to 650 nm.

The results of measuring binding profiles of hGH-A7 (●), hGH-A9 (○), and Pegvisomant (□) are shown in FIG. 4A. Further, the results of measuring binding profiles of hGH-A10 (▲), hGH-A11 (△), and Pegvisomant (□) are shown in FIG. 4C.

hGH-A7 and hGH-A9 were found to have high binding potency to hGH receptor, as compared with Pegvisomant. Further, hGH-A10 and hGH-A11 were found to have remarkably high binding potency to hGH receptor, as compared with Pegvisomant.

3. hGH Competitive Inhibitory Potency Analysis

Inhibitory potency of hGHRA-NexP on downstream signaling was analyzed by hGH competitive analysis. Serial dilutions of Examples 1 to 11 and Pegvisomant were added to each well of a 96-well plate containing hGHR/Luc/HEK293F, respectively. This plate was incubated in a 5% $C_2$ incubator at 37° C. for 24 hours. After incubation, 100 μL of luciferase assay reagent (Steady-Glo® luciferase assay system, Promega) was added to each well, and the plate was covered and protected from light. After 5 minutes at room temperature, a multi-mode microplate reader (SpectraMax M5, Molecular Devices) was used to analyze luminescence from wells.

The results of measuring binding profiles of hGH-A7 (●), hGH-A9 (○), and Pegvisomant (□) are shown in FIG. 4B. Further, the results of measuring binding profiles of hGH-A10 (▲), hGH-A11 (△), and Pegvisomant (□) are shown in FIG. 4D.

hGH-A7 and hGH-A9 were found to have high hGH competitive inhibitory potency, as compared with Pegvisomant. Further, hGH-A10 and hGH-A11 were found to have remarkably high hGH competitive inhibitory potency, as compared with Pegvisomant.

The results of measuring the relative binding potency and hGH competitive inhibitory potency of hGH-A1 to hGH-A11 and Comparative Example Pegvisomant are shown in Table 4, below. These results were plotted in FIG. 5.

TABLE 4

| Test sample | Relative binding potency | Relative inhibitory potency |
|---|---|---|
| Pegvisomant | 1.000 | 1.000 |
| hGH-A1 | 0.226 | 0.074 |
| hGH-A2 | 0.234 | 0.069 |
| hGH-A3 | 0.925 | 0.957 |
| hGH-A4 | 2.305 | 1.222 |
| hGH-A5 | 0.767 | 0.769 |
| hGH-A6 | 3.373 | 1.424 |
| hGH-A7 | 4.733 | 1.841 |
| hGH-A8 | 4.642 | 1.418 |
| hGH-A9 | 4.579 | 1.887 |
| hGH-A10 | 6.085 | 17.70 |
| hGH-A11 | 9.949 | 17.34 |

As shown in Table 4, hGH-A4, hGH-A6, hGH-A7, hGH-A8, hGH-A9, hGH-A10, and hGH-A11 showed high hGH receptor binding potency and competitive inhibitory potency, as compared with the known Pegvisomant. In particular, hGH-A10 and hGH-A11, each prepared by fusing NexP to the N-terminus of the variant, showed remarkably high competitive inhibitory potency.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

What is claimed is:

1. A growth hormone receptor antagonist comprising a growth hormone variant, wherein the amino acid sequence of the growth hormone comprises the substitutions of the 120th amino acid from the N-terminus with lysine, the 21st amino acid from the N-terminus with asparagine, the 174th amino acid from the N-terminus with serine, the 46th amino acid from the N-terminus with lysine, the 18$^{th}$ amino acid from the N-terminus with aspartic acid, and substitution of the 179$^{th}$ amino acid from the N-terminus with threonine.

2. The growth hormone receptor antagonist of claim 1, wherein the growth hormone receptor antagonist consists of the amino acid sequence of SEQ ID NO: 9.

3. The growth hormone receptor antagonist of claim 1, wherein a long-acting carrier is linked to the growth hormone variant.

4. The growth hormone receptor antagonist of claim 3, wherein the long-acting carrier is fused to the N-terminus or the C-terminus of the growth hormone variant.

5. The growth hormone receptor antagonist of claim 3, wherein the long-acting carrier is selected from the group consisting of polyethylene glycol, fatty acids, albumin or fragments thereof, albumin-binding substances, alpha-1 antitrypsin or variants thereof, immunoglobulin Fc or fragments thereof, a polymer of repeating units of a specific amino acid sequence, antibodies or fragments thereof, FcRn-binding substances, in vivo connective tissues or derivatives thereof, nucleotides, fibronectin, transferrin, saccharides, and polymers.

6. The growth hormone receptor antagonist of claim 5, wherein the long-acting carrier is an alpha-1 antitrypsin or a variant thereof.

7. The growth hormone receptor antagonist of claim 6, wherein the alpha-1 antitrypsin variant comprises substitution of one or more amino acids with another amino acid, and the substitution comprises substitution at one or more positions among the 1$^{st}$ and 25$^{th}$ amino acids from the N-terminus.

8. The growth hormone receptor antagonist of claim 6, wherein the alpha-1 antitrypsin variant comprises any one or more substitutions selected from the group consisting of substitution of the 9$^{th}$ amino acid from the N-terminus with asparagine, substitution of the 232$^{nd}$ amino acid from the N-terminus with serine, substitution of the 37$^{th}$ amino acid from the N-terminus with asparagine, and substitution of the 359$^{th}$ amino acid from the N-terminus with threonine.

9. The growth hormone receptor antagonist of claim 3, wherein the growth hormone variant is fused with the long-acting carrier directly or via a linker.

10. The growth hormone receptor antagonist of claim 9, wherein the linker is a peptidyl linker or a non-peptidyl linker.

11. The growth hormone receptor antagonist of claim 10, wherein the non-peptidyl linker is polyethylene glycol, polypropylene glycol, a copolymer of ethylene glycol and propylene glycol, polyoxyethylated polyol, polyvinyl alcohol, polysaccharide, dextran, polyvinyl ethyl ether, polylactic acid (PLA), polylactic-glycolic acid (PLGA), a lipid polymer, chitins, hyaluronic acid, or a combination thereof.

12. The growth hormone receptor antagonist of claim 10, wherein the peptidyl linker comprises two or more amino acids.

13. A pharmaceutical composition for preventing or treating a disease caused by human growth hormone, comprising the growth hormone receptor antagonist of claim 1.

14. The pharmaceutical composition of claim 13, wherein the disease is selected from the group consisting of acromegaly, gigantism, cancer, diabetic nephropathy, arthritis, lung inflammation, growth hormone deficiency (GHD), idiopathic short stature, Turner's syndrome, Prader-Willi syndrome, small for gestational age, and chronic renal insufficiency (CRI).

15. A method of preparing a growth hormone receptor antagonist, the method comprising the step of culturing cells comprising a polynucleotide encoding the growth hormone variant of claim 1.

* * * * *

SEQUENCE LISTING

<160> NUMBER OF SEQ ID NOS: 10

<210> SEQ ID NO 1
<211> LENGTH: 191
<212> TYPE: PRT
<213> ORGANISM: Artificial Sequence
<220> FEATURE:
<223> OTHER INFORMATION: hGH-A1 growth hormone with substitutions

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 2
<211> LENGTH: 191
<212> TYPE: PRT
<213> ORGANISM: Artificial Sequence
<220> FEATURE:
<223> OTHER INFORMATION: hGH-A2 growth hormone with substitutions

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

```
Leu Leu Lys Asp Leu Glu Glu Arg Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 3
<211> LENGTH: 191
<212> TYPE: PRT
<213> ORGANISM: Artificial Sequence
<220> FEATURE:
<223> OTHER INFORMATION: hGH-A3 growth hormone with substitutions

<400> SEQUENCE: 3

Phe Pro Thr Ile Pro Leu Ser Arg Leu Phe Asp Asn Ala Met Leu Arg
1               5                   10                  15

Ala His Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Ser Thr Phe
                165                 170                 175

Leu Arg Ile Val Gln Cys Arg Ser Val Glu Gly Ser Cys Gly Phe
            180                 185                 190

<210> SEQ ID NO 4
<211> LENGTH: 191
<212> TYPE: PRT
<213> ORGANISM: Artificial Sequence
<220> FEATURE:
<223> OTHER INFORMATION: hGH-A4 growth hormone with substitutions

<400> SEQUENCE: 4

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45
```

```
Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
                100                 105                 110

Leu Leu Lys Asp Leu Glu Glu Lys Ile Gln Thr Leu Met Gly Arg Leu
            115                 120                 125

Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Ser Thr Phe
                165                 170                 175

Leu Arg Thr Val Gln Cys Arg Ser Val Glu Gly Ser Cys Gly Phe
            180                 185                 190

<210> SEQ ID NO 5
<211> LENGTH: 191
<212> TYPE: PRT
<213> ORGANISM: Artificial Sequence
<220> FEATURE:
<223> OTHER INFORMATION: hGH-A5 growth hormone with substitutions

<400> SEQUENCE: 5

Phe Pro Thr Ile Pro Leu Ser Arg Leu Phe Asp Asn Ala Met Leu Arg
 1               5                  10                  15

Ala His Arg Leu Asn Gln Leu Ala Phe Asp Thr Tyr Gln Glu Phe Glu
                 20                  25                  30

Glu Ala Tyr Ile Pro Lys Glu Gln Lys Tyr Ser Phe Leu Gln Asn Pro
             35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
                100                 105                 110

Leu Leu Lys Asp Leu Glu Glu Lys Ile Gln Thr Leu Met Gly Arg Leu
            115                 120                 125

Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Ser Thr Tyr
                165                 170                 175

Leu Arg Ile Val Gln Cys Arg Ser Val Glu Gly Ser Cys Gly Phe
            180                 185                 190

<210> SEQ ID NO 6
<211> LENGTH: 191
<212> TYPE: PRT
<213> ORGANISM: Artificial Sequence
```

```
<220> FEATURE:
<223> OTHER INFORMATION: hGH-A6 growth hormone with substitutions

<400> SEQUENCE: 6

Phe Pro Thr Ile Pro Leu Ser Arg Leu Phe Asp Asn Ala Met Leu Arg
1               5                   10                  15

Ala His Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Pro Ser Glu Ser Ile Pro Thr Pro Ser Asn Lys
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Ser Thr Tyr
                165                 170                 175

Leu Arg Ile Val Gln Cys Arg Ser Val Glu Gly Ser Cys Gly Phe
            180                 185                 190

<210> SEQ ID NO 7
<211> LENGTH: 191
<212> TYPE: PRT
<213> ORGANISM: Artificial Sequence
<220> FEATURE:
<223> OTHER INFORMATION: hGH-A7, hGH-A10 growth hormone with
      substitutions

<400> SEQUENCE: 7

Phe Pro Thr Ile Pro Leu Ser Arg Leu Phe Asp Asn Ala Met Leu Arg
1               5                   10                  15

Ala His Arg Leu Asn Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Pro Ser Glu Ser Ile Pro Thr Pro Ser Asn Lys
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140
```

-continued

```
Lys Phe Asp Thr Asn Ser His Asn Asp Asp Ala Leu Leu Lys Asn Tyr
145                 150                 155                 160

Gly Leu Leu Tyr Cys Phe Asn Lys Asp Met Ser Lys Val Ser Thr Tyr
                165                 170                 175

Leu Arg Ile Val Gln Cys Arg Ser Val Glu Gly Ser Cys Gly Phe
            180                 185                 190

<210> SEQ ID NO 8
<211> LENGTH: 191
<212> TYPE: PRT
<213> ORGANISM: Artificial Sequence
<220> FEATURE:
<223> OTHER INFORMATION: hGH-A8 growth hormone with substitutions

<400> SEQUENCE: 8

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe
            180                 185                 190

<210> SEQ ID NO 9
<211> LENGTH: 191
<212> TYPE: PRT
<213> ORGANISM: Artificial Sequence
<220> FEATURE:
<223> OTHER INFORMATION: hGH-A9, hGH-A11 growth hormone with
      substitutions

<400> SEQUENCE: 9

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
                20                  25                  30

Glu Ala Tyr Ile Pro Lys Glu Gln Lys Tyr Ser Phe Leu Lys Asn Pro
            35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
```

```
                65                  70                  75                  80
Leu Leu Ile Gln Ser Trp Leu Glu Pro Val Gln Phe Leu Arg Ser Val
                    85                  90                  95
Phe Ala Asn Ser Leu Val Tyr Gly Ala Ser Asp Ser Asn Val Tyr Asp
                    100                 105                 110
Leu Leu Lys Asp Leu Glu Glu Lys Ile Gln Thr Leu Met Gly Arg Leu
                    115                 120                 125
Glu Asp Gly Ser Pro Arg Thr Gly Gln Ile Phe Lys Gln Thr Tyr Ser
                    130                 135                 140
Lys Phe Asp Thr Asn Ser His Asn Asp Asp Ala Leu Leu Lys Asn Tyr
145                 150                 155                 160
Gly Leu Leu Tyr Cys Phe Arg Lys Asp Met Asp Lys Val Ser Thr Phe
                    165                 170                 175
Leu Arg Thr Val Gln Cys Arg Ser Val Glu Gly Ser Cys Gly Phe
                    180                 185                 190

<210> SEQ ID NO 10
<211> LENGTH: 394
<212> TYPE: PRT
<213> ORGANISM: Artificial Sequence
<220> FEATURE:
<223> OTHER INFORMATION: alpha-1 antitrypsin variant

<400> SEQUENCE: 10

Glu Asp Pro Gln Gly Asp Ala Ala Asn Lys Thr Asp Thr Ser His His
1               5                   10                  15
Asp Gln Asp His Pro Thr Phe Asn Lys Ile Thr Pro Asn Leu Ala Glu
                    20                  25                  30
Phe Ala Phe Ser Leu Tyr Arg Gln Leu Ala His Gln Ser Asn Ser Thr
                    35                  40                  45
Asn Ile Phe Phe Ser Pro Val Ser Ile Ala Thr Ala Phe Ala Met Leu
                50                  55                  60
Ser Leu Gly Thr Lys Ala Asp Thr His Asp Glu Ile Leu Glu Gly Leu
65                  70                  75                  80
Asn Phe Asn Leu Thr Glu Ile Pro Glu Ala Gln Ile His Glu Gly Phe
                    85                  90                  95
Gln Glu Leu Leu His Thr Leu Asn Gln Pro Asp Ser Gln Leu Gln Leu
                    100                 105                 110
Thr Thr Gly Asn Gly Leu Phe Leu Ser Glu Gly Leu Lys Leu Val Asp
                    115                 120                 125
Lys Phe Leu Glu Asp Val Lys Lys Leu Tyr His Ser Glu Ala Phe Thr
                    130                 135                 140
Val Asn Phe Gly Asp Thr Glu Glu Ala Lys Lys Gln Ile Asn Asp Tyr
145                 150                 155                 160
Val Glu Lys Gly Thr Gln Gly Lys Ile Val Asp Leu Val Lys Glu Leu
                    165                 170                 175
Asp Arg Asp Thr Val Phe Ala Leu Val Asn Tyr Ile Phe Phe Lys Gly
                    180                 185                 190
Lys Trp Glu Arg Pro Phe Glu Val Lys Asp Thr Glu Glu Glu Asp Phe
                    195                 200                 205
His Val Asp Gln Val Thr Thr Val Lys Val Pro Met Met Lys Arg Leu
                    210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
```

-continued

```
                    245                 250                 255
Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
            340                 345                 350

Leu Glu Ala Ile Asn Met Ser Ile Pro Pro Glu Val Lys Phe Asn Lys
        355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys
385                 390
```